United States Patent [19]

Oxley et al.

[11] Patent Number: 5,084,041
[45] Date of Patent: Jan. 28, 1992

[54] MULTICOMPARTMENT BIOLOGICAL FLUID SPECIMEN COLLECTION BAG

[75] Inventors: L. Thomas Oxley, Riverwoods; Virginia C. Morrisseau, Lindenhurst, both of Ill.

[73] Assignee: T Systems, Inc., Riverwoods, Ill.

[21] Appl. No.: 509,257

[22] Filed: Apr. 13, 1990

[51] Int. Cl.$^5$ ............... A61B 19/00; A61M 1/00
[52] U.S. Cl. .................... 604/410; 604/317; 604/408
[58] Field of Search ............ 206/438, 459, 807; 215/6, 230, 233, 247; 220/214, 20, 22, 22.5; 604/317-321, 409, 410

[56] References Cited

U.S. PATENT DOCUMENTS

| | | | |
|---|---|---|---|
| 3,011,918 | 10/1975 | Turner | 604/410 |
| 4,183,434 | 1/1980 | Watt | 206/438 |
| 4,188,989 | 2/1980 | Andersen | 604/410 X |
| 4,503,864 | 3/1985 | Powers | 604/317 |
| 4,650,082 | 3/1987 | Paciorek | 215/230 |
| 4,661,100 | 4/1987 | Rechsteiner | 604/318 |
| 4,684,426 | 8/1987 | Takayama | 215/230 |
| 4,711,372 | 12/1987 | Gach | 220/214 |
| 4,900,321 | 2/1990 | Kaufman et al. | 604/410 X |

FOREIGN PATENT DOCUMENTS

| | | | |
|---|---|---|---|
| 0253651 | 1/1988 | European Pat. Off. | 604/317 |
| 0225337 | 7/1985 | German Democratic Rep. | 604/318 |
| 2176096 | 12/1986 | United Kingdom | 604/317 |
| 8404036 | 10/1984 | World Int. Prop. O. | 604/317 |

Primary Examiner—David T. Isabella
Assistant Examiner—Elizabeth M. Burke
Attorney, Agent, or Firm—Reinhart, Boerner, Van Deuren, Norris & Rieselbach

[57] ABSTRACT

A plastic bag for collection of a human fluid specimen for chemical analysis and testing. The plastic bag includes a plurality of subcompartments for collecting a urine specimen and other biological specimens for analysis to ascertain the presence or controlled drug substances or other undesired chemicals or diseases. The plastic bag includes the features of a nonreusable plastic seal around each subcompartment containing redundant fluid specimens to enable a legally secure, reliable characterization of the fluid specimen.

15 Claims, 3 Drawing Sheets ns
MULTICOMPARTMENT BIOLOGICAL FLUID SPECIMEN COLLECTION BAG The present invention is concerned generally with a plastic bag for collection of a human fluid specimen for chemical analysis. More particularly, the invention is concerned with a multicompartment plastic bag for collecting urine and other biological specimens for analysis to ascertain the presence in a Person of controlled drug substances or of other undesired chemicals or diseases.

Analysis for harmful drugs, diseases and other undesirable substances in a human subject involves collection and analysis of a urine or other biological liquid specimen, typically initiated by collecting the specimen in a glass or hard plastic container. Labels are attached to the exterior of the container; and a lab technician includes on the label the subject's name, date of collection and other relevant data for use in analysis of the specimen. Analysis of the specimen using such a container requires additional preparatory steps, including (a) creation of a new record of information for each analytical procedure performed on the specimen, while also maintaining the legal chain of evidence for the specimen, (b) physical apportionment of the initially collected specimen into a plurality of specimens for a number of different analytical evaluations, and (c) maintenance of the sterility and chemical integrity of the specimen during and after subdivision into a plurality of specimens undergoing different tests in the analytical process. There is a strong and growing demand for large scale drug testing programs and disease analysis by various corporations, governmental agencies, and particularly for military personnel, transportation workers and construction workers in high risk occupations. Such a substantial increase in the demand for drug testing Programs will place a great premium on improved economics, efficiency and reliability, while requiring strict integrity of the legal chain of specimen custody.

It is therefore an object of the invention to provide an improved method and article of manufacture for collecting a human fluid specimen for ascertaining the presence of controlled drug substances and diseases.

It is another object of the invention to provide a novel multicompartment plastic bag for collecting human fluid specimens for chemical and disease control analysis.

It is a further object of the invention to provide an improved plastic bag for collecting a human fluid specimen and apportioning the specimen among a plurality of selectable sections or compartments of the bag.

It is an additional object of the invention to provide a novel multicompartment plastic bag having a writeable identification element area for entering information to maintain the chain of custody of a human fluid specimen collected for drug analysis.

It is yet another object of the invention to provide an improved multicompartment plastic bag having a sealed edge with holes punched therein for hanging the bag on a rack or transporting the bag as part of the specimen processing steps.

It is still a further object of the invention to provide a novel plastic bag with a selectable pattern of lines imprinted on the bag, each line pattern characteristic of a heat sealable design to define the analytically desired bag compartments in which to collect fluid specimens.

It is yet a further object of the invention to provide an improved multicompartment plastic bag for collecting human fluid specimens and performing selected pre-screening tests within predetermined bag sections.

It is an additional object of the invention to provide a novel plastic bag for collecting and subdividing human fluid specimens and preserving the fluid specimen integrity using embedded tampering indicators for the bag, such as a tamper evident seal.

It is yet another object of the invention to provide an improved plastic bag with pouch or pocket elements at selected locations for providing an enlarged specimen volume and increased specimen optical path length for analytical procedures.

It is still a further object of the invention to provide a novle multicompartment plastic bag having a rigid or semirigid element disposed within a selected bag section and allowing analysis of the specimen in the bag section by various types of analytical equipment matingly receiving the shape of the rigid element.

It is still an additional object of the invention to provide an improved individual plastic bag adapted to receive fluid specimens from an open top or bottom having a semi rigid element in this sealable bag and enabling use as a pipette, cuvette or test tube.

Other objects, features and advantages of the present invention will be readily apparent from the following description of the preferred embodiments thereof, taken in conjunction with the accompanying drawings described below wherein like elements have like numerals throughout the several views.

DETAILED DESCRIPTION OF PREFERRED EMBODIMENTS

Figure 1:
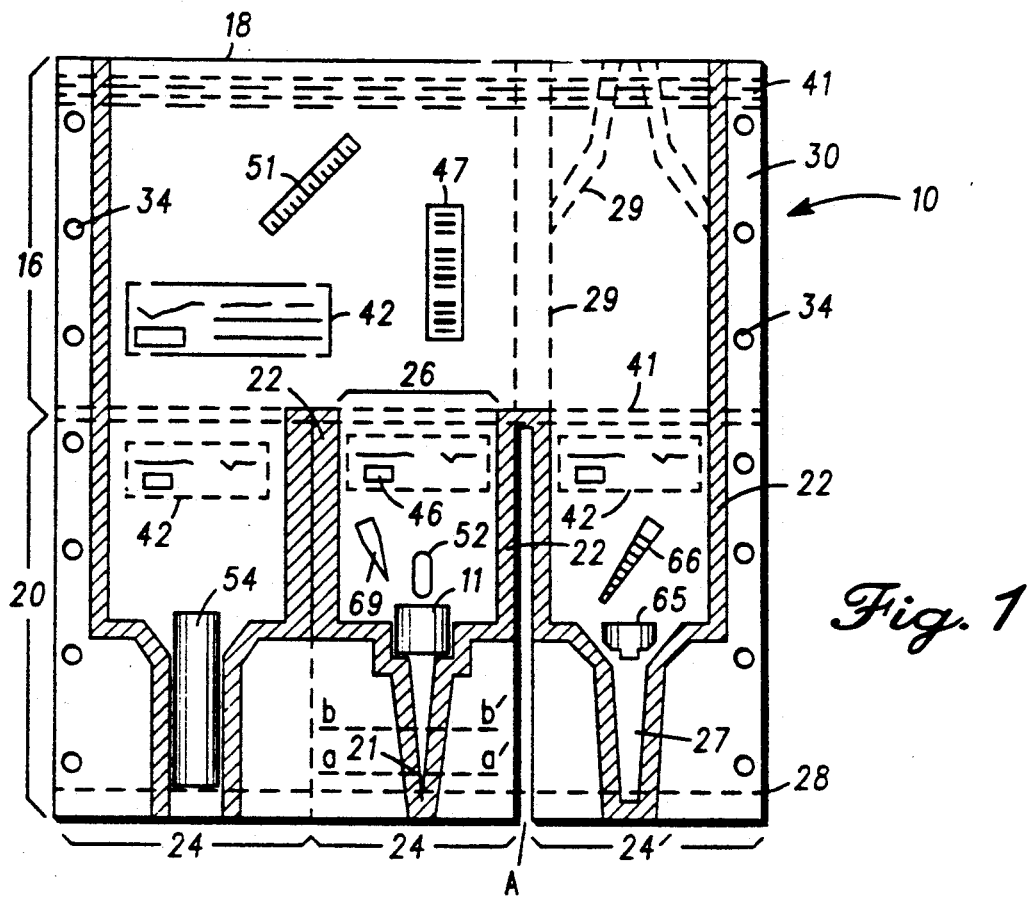
FIG. 1 is a front elevation of a multicompartment plastic bag constructed in accordance with the invention.

Referring to the drawings and in particular to FIGS. 1 and 2, a multicompartment plastic bag constructed in accordance with the invention is indicated generally at 10. Collection and analysis of a human fluid specimen is accomplished by utilizing the illustrated multicompartment plastic bag 10 (hereinafter "the plastic bag 10"). In order to carry out determination of the presence of a drug, controlled substance or disease in a person, the plastic bag 10 functions first to collect a fluid specimen taken from the subject, such as a urine specimen. Various means can be used to effectuate collection of the fluid specimen. For example, urine collection can be accomplished as shown in FIG. 3 by using a funnel 12 and container 14 having the plastic bag 10 disposed within the container 14 for receiving the urine. The plastic bag 10 includes an upper bag section 16 having an opening at one end (shown generally as 18 in FIG. 1) to enable receiving the fluid specimen. This is accomplished by inserting the plastic bag 10 into the container 14 with the open end 18 positioned at the top of the container 14. The funnel 12 is then pushed into the container 14, and the plastic bag 10 is in position to receive and accumulate the fluid specimen. Also note the plastic bag 10 can include a collection overflow edge 15 which is curled upward to catch any fluid specimen during accumulation or transport of the specimen in the bag 10. Once the fluid specimen has been collected in the plastic bag 10, the funnel 12 can be removed and discarded. While the plastic bag 10 is still within the container 14, or alternatively after removal of the plastic bag 10 from the container 14, the accumulated fluid specimen can be moved within the upper bag section 16 to apportion the fluid specimen. This fluid apportionment can take place in both the upper bag section 16 and selected portions of the lower bag section 20. In the preferred embodiment the plastic bag 10 can be heat sealed at the top to preserve the specimen integrity before apportioning the specimen in the various bag sections. In an alternative embodiment one can choose to apportion the fluid specimen between the bag sections before sealing.

The ability to apportion the fluid specimen among the various bag sections enables establishing a plurality of different specimens for scientific reliability and legal requirements. The apportionment also can be useful if some prescreening tests are to be done on the fluid specimen to eliminate the need to perform complete testing on a large number of specimens.

Figure 2A:
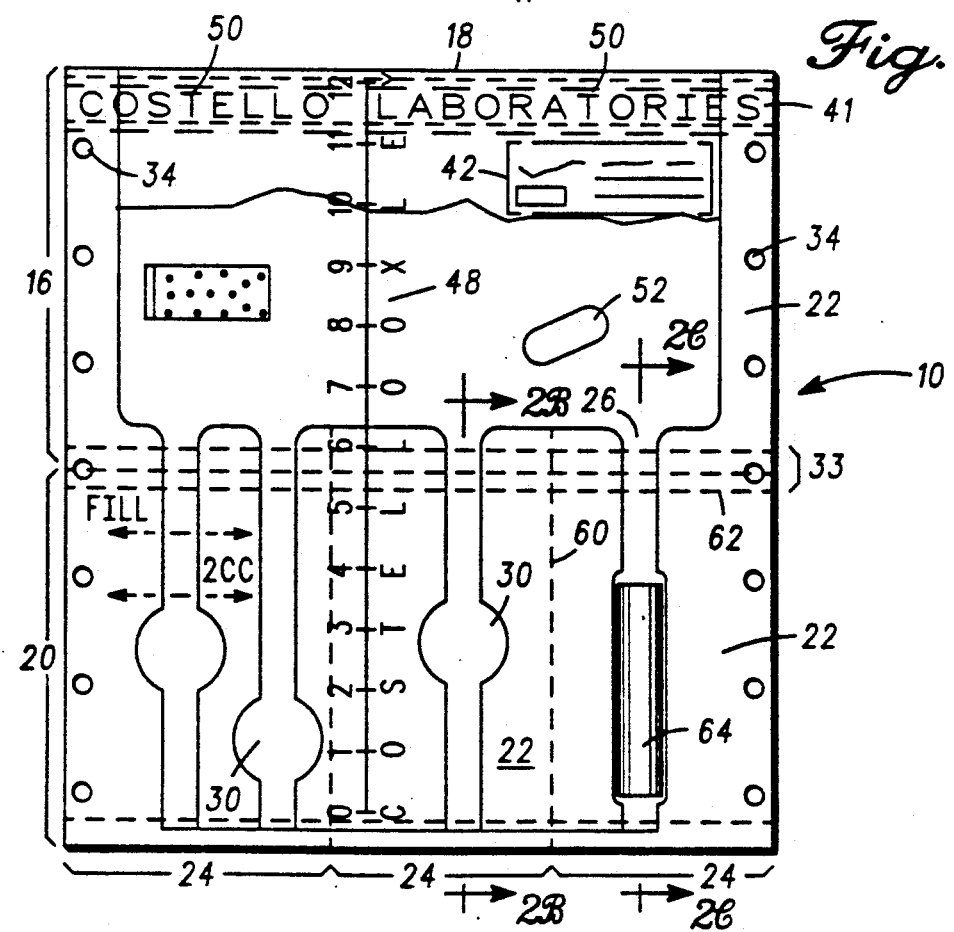
FIG. 2A illustrates a front elevation of a multicompartment plastic bag having a plurality of pouch or pocket elements.
Figure 3A:
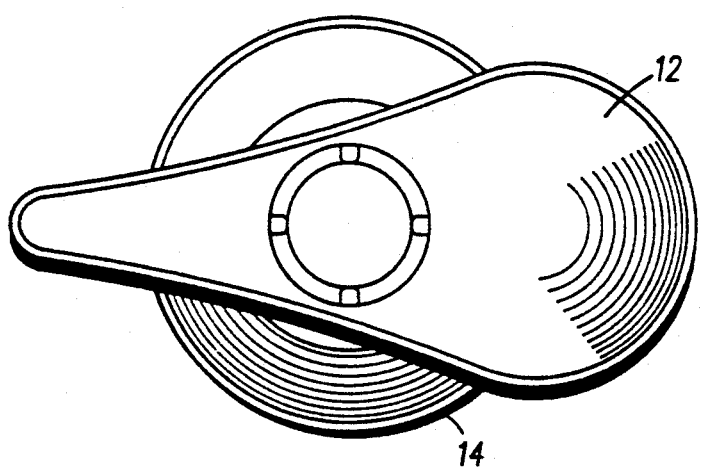
FIGS. 3A and 3B show a funnel and container holding the multicompartment plastic bag for receiving and collecting a human urine specimen.
Figure 3B:
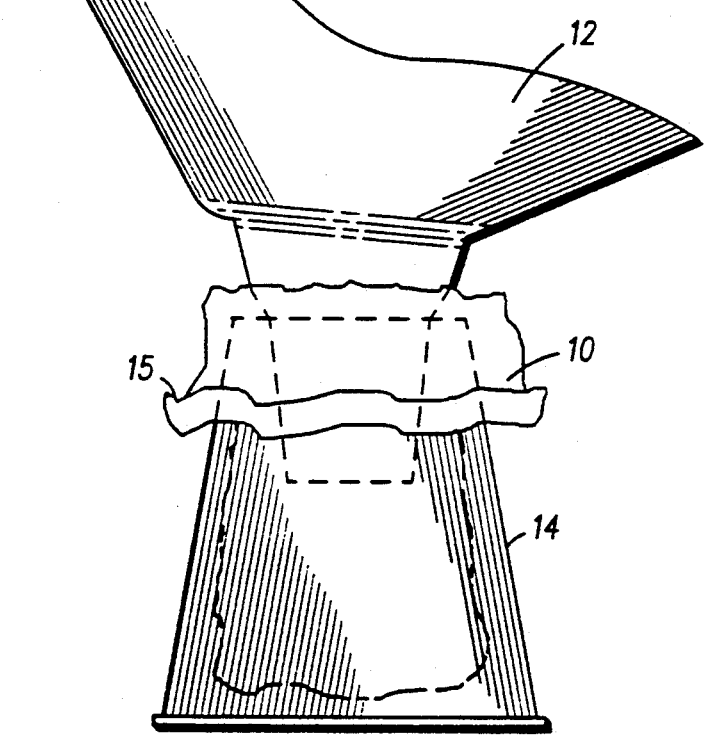

To accomplish the apportionment of the specimen within the various bag sections, the lower bag section 20 is at least partially open to the upper bag section 16 via opening 26 as shown in FIG. 2A once the fluid specimen is apportioned. These openings are defined by means of the location of cross-hatched seal areas 22 in the lower bag section 10 shown in FIG. 1. In the preferred embodiment these seal areas 22 have been heat sealed by the manufacturer prior to shipment to the customer and accomplished by use of any one of a variety of conventional available devices for heat sealing plastic. Thus, the bag design can accommodate various subcompartments 24 in the lower bag section 20 and provide the opening 26 between the upper and lower bag sections, 16 and 20, respectively. One can also use the seal areas 22 to provide different design configurations of subcompartments and even provide additional shapes adjunct to the subcompartments, such as a spout 27 for each of the subcompartments 24 (see FIG. 1). The spout 27 is usable by merely cutting along one line chosen anywhere above a lower seal line 28 and across the mouth of the spout 27.

In addition to the illustrated layout for the bag seal areas 22 provided by the manufacturer, the customer, or even the analytical laboratory user, can select alternative seal designs which can be implemented by various known means. A customer can thus select and prepare a custom design by using a predetermined bag size and a conventional manually operating heat sealing device 36 (see FIG. 4C) having a seal bar design in the intended geometry of the final seal areas 22. The plastic bag 10 can therefore include a plurality of different optional heat seal line patterns 29 (see FIG. 1) disposed on at least one of the plastic sheets comprising the plastic bag 10. One can, for example, use different seal line markings (dashed, dotted, and color encoded) to denote different available seal patterns. The various heat seal line patterns 29 can then be implemented by, for example, (a) using manually guided heat seal means, (b) using the heat sealing device 36 having an appropriate seal design pattern (described above) or (c) employing a conventional machine control system to perform heat seal line tracing which seals along one of the given marked seal line patterns 29.

Figure 2B:
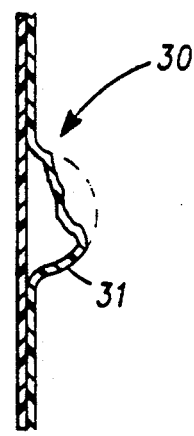
FIG. 2B is a side elevation taken along line 2B—2B of the plastic bag shown in FIG. 2A.
Figure 2C:
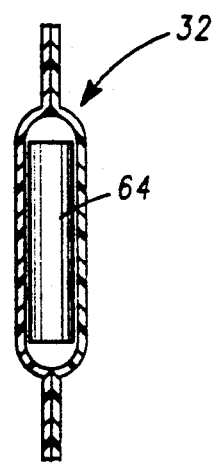
FIG. 2C is a side elevation taken along lines 2C—2C in FIG. 2A.

The ability to construct a variety of functional shapes from the plastic bag 10 can further include, for example, a pipette design 21 in FIG. 1. Once the opening 26 has been sealed to form a subcompartment 24 filled with a fluid specimen, the pipette design 21 allows dispensing small fluid specimen portions. This can be done by first cutting along the lower seal line 28 (or along lines aa' or bb' for larger openings). Tubing 11 provides support for the surrounding plastic bag 10 and enables controllably displacing fluid in the subcompartment 24 and dispensing small portions of the fluid specimen for testing. Such a pipette shape can be combined with other conceivable designs to enhance bag operation and analysis of the fluid specimen. Further useful shapes can also include, for example, a pocket or pouch element 30 in the lower bag section 20 (see FIG. 2). This pouch element 30 is defined by at least one plastic layer portion 31 being discontinuous relative to the plane of the plastic sheets of the plastic bag 10. That is, as best seen in FIG. 2B, the pouch element 30 includes the layer portion 31 which deviates from the relatively smooth surface defined by the twin sheets forming the plastic bag 10. The pouch element 30 is fillable with the fluid specimen to provide a locally enlarged specimen volume and increased specimen optical path length. This structural feature therefore allows accumulation of sufficient specimen quantities to perform analytical procedures not normally accomplishable with the relatively thin layers and unknown layer thicknesses of fluid specimens present within the plastic bag 10.

Additional functional shapes therefore allow well controlled analysis of known specific volumes and known particular optical path lengths of the fluid specimen. The analytical technician can also easily remove, by means such as a syringe or pipette, a substantial and known volume of a fluid specimen. To this end the plastic bag 10 also lends itself to inclusion of various precise volume indicators imprinted in association with the pouch element 30 (see, for example, FIG. 2A left most subcompartment 24 with the 2cc indicator marking).

Other shapes can also be fabricated, such as a cylindrical pouch 32 (see FIG. 2C), in order to provide a fit within mating recepticals of various types of conventional analytical equipment, such as apparatus originally designed to analyze fluid specimens retained within conventional test tubes or other conventional sample containers. The cylindrical pouch 32 can further include rigid or semi rigid shapes, such as a cylindrical tube. Further details of this advantageous shape feature will be described with more particularly hereinafter.

The subcompartments 24 defined by the design of the plastic bag 10 can be selectively filled in the manner described hereinbefore: the technician can move the fluid specimen between the upper bag section 16 and lower bag section 20 and then through the openings 26 into each of the desired subcompartments 24. Either before or after the technician has apportioned the fluid specimen in the desired sections of the plastic bag 10, the conventional plastic sealing device 36 (see FIG. 4C) can be used to seal the lower bag section 20. This is accomplished by heat sealing along center seal area 33 as shown in FIG. 2A. In addition as described hereinbefore, the plastic bag 10 can be completely closed by heat sealing the upper seal area 37.

The technician can commence the specimen analysis process by separating selected ones of the subcompartments 24 and the upper bag section 16. Separation can be accomplished by, for example, cutting with scissors or separating along a prepared tear line. In another form of the invention the subcompartments 24 can be removed by merely cutting along one line since they are already separated by the manufacturer along another line (see open area denoted A for subcompartment 24 in FIG. 1).

Figure 4A:
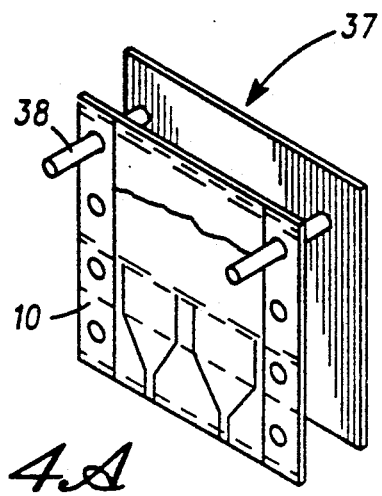
FIG. 4A illustrates a support or storage rack for holding a multicompartment plastic bag.
Figure 4B:
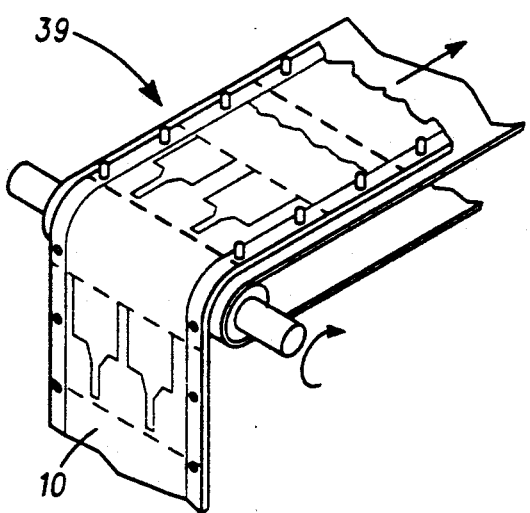
FIG. 4B shows a conveyor system for transporting the plastic bag for analysis of the fluid specimen contained therein and FIG. 4C shows a heat sealing device for closure of the plastic bag and forming selected heat seal areas on the plastic bag.
Figure 4C:
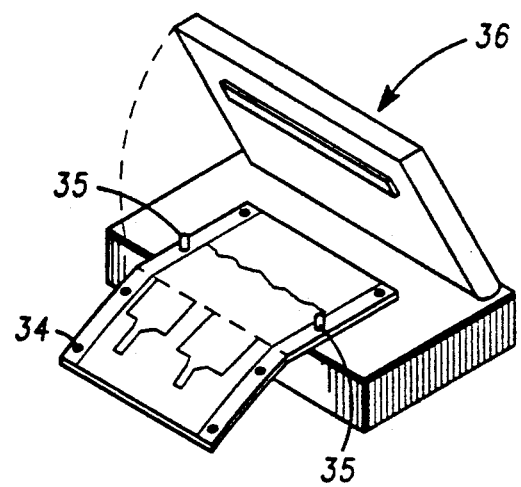

In a preferred form of the invention, the plastic bag 10 also includes holes 34 punched in the perimeter seal region 30 of the plastic bag 10 (see FIG. 1). The holes 34 can be used to assist in expediting evaluation of the fluid specimen in the plastic bag 10. For example, the plastic bag 10 can be hung on locating pins 35 of the heat sealing device 36 (see FIG. 4C). In addition, as shown in FIG. 4A the holes 34 allow hanging the plastic bag 10 on a storage rack 37 having one or more hanging rods 38 to await specimen analysis or for long term refrigerated or frozen storage. Such a storage rack 36 conserves storage space allowing large numbers of specimens to be maintained in a very small volume. The holes 34 also enable coupling of the plastic bag 10 to a conveyor system 39 for transport and subsequent analysis of the fluid specimen (see FIG. 4B).

The plastic bag 10 is preferably an optically transparent or visually translucent material allowing use of any one of a variety of conventional optical analysis procedures on the fluid specimen. Such optical analysis procedures can include, for example, simple naked eye observations and optical absorption spectrophotometry.

The plastic bag 10 also should be inert to the fluid specimen contained therein to avoid chemical modification or contamination. The plastic bag 10 should further allow long-term cold storage and freezing, while maintaining the physical and chemical integrity of the fluid specimen. Numerous conventional thermoplastic materials fulfill these requirements and examples of such materials are "Saran" coated polyester with an exterior coating of polyethylene.

As mentioned generally before, the ability to collect the fluid specimen in the upper bag section 16 and in various ones of the subcompartments 24 enables performance of a plurality of different tests and maintenance of a reference standard and backup standards. The upper bag section 16, for example, can be used for holding a specimen for preliminary screening or overflow. The specimens in the subcompartments 24 can, for example, be used for preliminary, primary and confirmatory analyses and also for long-term backup specimens.

The ability to use numerous specimens allows a thorough analysis of the specimen. The ability to have a backup specimen(s) provides a sound evidentiary position when needed to legally and scientifically establish the presence of drugs, diseases, controlled substances or other undesirable chemicals in a human subject.

Scientific objectives for specimen analysis are met by virtue of the redundancy of available specimens, the performance of multiple specimen analyses and maintenance of a reference or backup specimen. Legal objectives are met by providing clear evidence of the identity of a specimen and unbroken chain of custody over the cycle of collection of the specimen and the performance of numerous analytical procedures. This custodial objective is accomplished in part by inclusion of an identification element on a surface of the plastic bag 10. The identification element can be, for example, a writeable area 42 for entering information identifying the specimen donor, a signature box for the donor and locations for entry of the identity and signature of each party in the chain of specimen custody. This writeable area 42 also is preferably on each of the separate sections of the Plastic bag 10 in order to establish identity and custody of each specimen portion. Additional identification can be Provided by other means, such as, by bar code serial numbers 46 or labels 47 attached to, or imprinted on, each of the separable bag subcompartments 24 and/or on the upper bag section 16 (see FIG. 1).

In order to prevent tampering with the fluid specimen once it has been collected, the plastic bag 10 includes a first tampering indicator means which can be an embossed or imprinted code 50 along the top seal area 41 of the plastic bag 10 (see FIG. 2A). Such a tampering indicator can be applied after collecting the specimen in conjunction with heat seal closure of the bag 10 by use of the heat sealing device 36 shown in FIG. 4C. In another aspect of the invention the tampering indicator means can extend from the upper bag section 16 to the lower bag section 20. Another such tampering indicator can be, for example, an indelible marking 48 on the plastic bag 10. The tampering indicators 48 and 50 of FIG. 2A exhibit a low symmetry design, such as, a name and a precision line having numerical or letter indicators disposed along the line. Alternatively, a more complex shape or design can be embodied in the bag sheets, such as a personalized "seal" having an appearance which would be notable altered if the plastic bag 10 were tampered with before technician analysis. As in the case of the identifying writeable area 42, such tampering indicators can be included with each of the separate subcompartments 24 or on the upper bag section 16 in order to minimize the opportunity for any tampering occurring at any stage of the specimen analysis.

In another aspect of the invention, certain prescreening tests can be performed on the fluid specimen in order to diminish the number of "suspect" specimens which must undergo more detailed and costly analysis. Such a prescreening test can be performed on the fluid specimens collected in any of the subcompartments 24 of the plastic bag 10. As described hereinbefore in the preferred embodiment, the specimens are apportioned in the subcompartments 24 after the upper bag section 16 is sealed from the outside environment. Once the specimens are apportioned, the subcompartments 24 are sealed and isolated from each other and also from the upper bag section 16. Isolation of the various fluid specimens also enables testing to proceed wholely within the bag which also diminishes the possibility of contamination of the specimen or of disease transmission to a technician preforming the analysis.

Prescreening procedures can involve simple tests, such as, checking the temperature of the fluid specimen by use of a conventional thermal strip indicator 51 (see FIG. 1) or checking pH of the specimen by the use of pH sensitive indicator strips. More complicated prescreening can involve the release of one or more analytical reagents in the upper bag section 16, such as, by opening or breaking a capsule 52 containing an analytical agent (see FIG. 2A). This analytical reagent reacts with the fluid specimen and analytical equipment (not shown) can then be used to carry out the prescreening tests. For example, Enzyme Immunoassay (EIA) can be performed by prefilling two capsules 52, one with reagent A and the other with reagent B, and sealing such capsules. At the time of specimen collection, the two capsules 52 (including the reagents A and B for determining the presence of a specific drug) are inserted into selected parts of the upper bag section 16 or the lower bag section 20. After the specimen has been collected, and the bag sections 16 and 20 sealed from one another, analysis can proceed in the selected bag section by fracturing the capsules 51. The reagents A and B contained in each of the capsules 52 are then released to react with the fluid specimen. The reaction can generate a color change which is related to the drug concentration in the specimen. This color change can be detected through the optically transparent bag section 16 or 20, either by the naked eye or analyzed in detail by a conventional optical instrument, such as a spectrophotometer (not shown). Separate selected pairs of reagents in the capsules 52 are typically used for detecting each individual drug. Multiple ones of the subcompartment 24 can be provided in the bag sections 16 or 20, each intended for pairs of the capsules 52 for a different drug analysis. Alternately, a single fracturable multi-compartmented capsule 52 having numerous reagent pairs can be provided in the bag sections 16 or 20. Other conventional prescreening chemical tests are also possible, such as, for example, radio immunassay analysis, fluorescence polarization immunoassy testing or a modified thin layer chromatography option.

In another form of the invention, the plastic bag 10 further includes a substantially rigid element which can be disposed loosely in at least one particular portion of the bag. For example, the rigid element can be a piece of cylindrical tubing 54, a sample cup 65, or a conical pipette 66, as shown in FIG. 1. One can also choose to have a snug fit for the lower portion of the cylindrical tubing 54, the sample cup 65, or the conical pipette 66 in order to establish a seal to the bag 10. This seal surface will allow specimen handling such that no leakage of the fluid specimen occurs other than by a path through the tubing 54, the sample cup 65 or the pipette 66.

Figure 5:
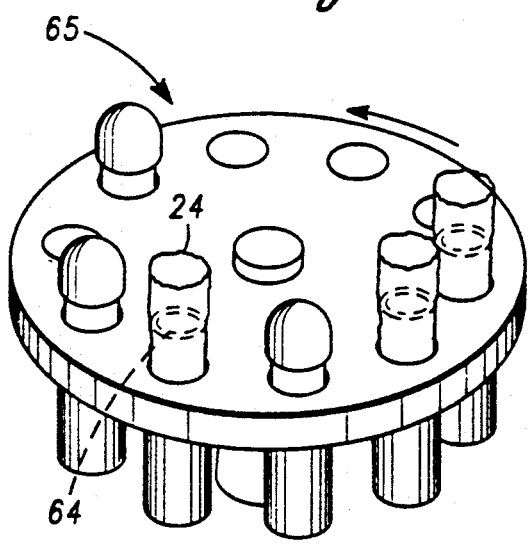
FIG. 5 illustrates a carousel style analytical apparatus having cylindrical receptacles for receiving plastic bag subcompartments.

Such a rigid or semi-rigid element structure advantageously also provides a predetermined shape for allowing shape sensitive mechanical handling of the fluid specimen. By establishing this predetermined shape, the specimen can be handled by analytical processes which require fitting the bag portion which holds the specimen into a mating receptacle of the analytical instrument. For example, in the case of the rigid or semi-rigid element being the cylindrical tubing 64 (see FIG. 2A), the fluid specimen is collected in the right most bag subcompartment 24 which is separated from the plastic bag 10 by cutting along seal lines 60 and 62. The separated bag subcompartment 58 containing the fluid specimen and the cylindrical tubing 54 can then be directly inserted into conventional test tube receptacles of a carousel style specimen processing station 65 (see FIG. 5). Using such an analytical processing station, an automated specimen sampling probe or syringe is lowered to retrieve a sample of the fluid specimen for chemical analysis. Therefore, the substantially rigid cylindrical tubing 64 allows the unmodified use of conventional fluid specimen processing equipment for analysis of specimens collected in the plastic bag 10 of the invention. The size and shape of the rigid element can be adjusted for the amount of fluid or biological specimen collected.

In another aspect of the invention the multicompartment plastic bag 10 can enclose various useful tools, such as, probe 70 in FIG. 1 for puncturing the spout of the pipette 21 to provide highly controllably release of the fluid specimen or for breaking the capsule 52 used for in situ chemical analysis.

Figure 6A:
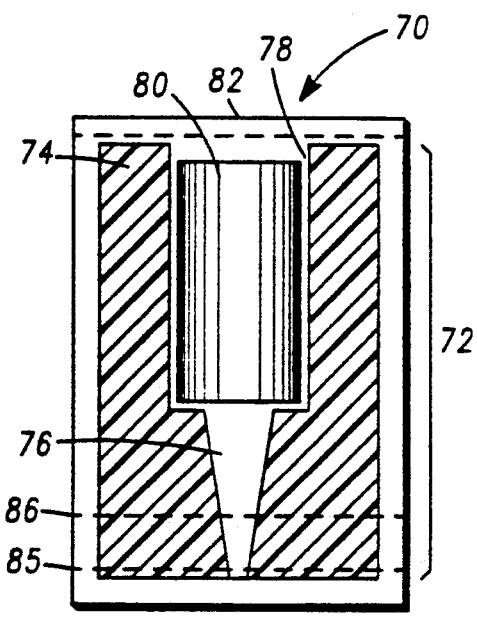
FIG. 6A shows an individual plastic bag containing a semi-rigid element.

In another form of the invention shown in FIG. 6, an individual plastic bag 70 incorporates advantageous structural elements enabling use for example, as a pipette, test tube and cuvette in fluid specimen analysis. This individual plastic bag 70 can be supplied individually or can be provided as a separable part of the multicompartment plastic bag 10 described hereinbefore. The structural elements included in the individual plastic bag 70 comprise, e.g., a pipette 72 in FIG. 6A. The pipette 72 is constructed by forming heat seal areas 74 in the individual plastic bag 70 to define a conical pipette section 76 and an upper pipette section 78. Within the upper pipette section 78 is disposed a semi-rigid or displaceable component, such as conventional plastic tubing 80. In the embodiment of FIG. 6A the fluid specimen is introduced through an open top 82 which is then heat sealed to enclose the fluid specimen. This fluid specimen can later be analyzed, and the technician can use the pipette 72 by cutting along one of lines 85 or 86, depending on the fluid flow rate desired. The technician can thus dispense the fluid specimen by squeezing the displaceable tube 80 causing controlled fluid removal for analysis.

The plastic bag 70 can also be presealed along the top 82, and the bottom is open to the conical pipette section 76. In such a configuration the fluid specimen can be drawn into the individual plastic bag 70 by squeezing the displaceable tube 80, causing a suction action drawing in the fluid specimen. The individual plastic bag 70 can then be sealed and subsequent specimen analysis performed.

Figure 6B:
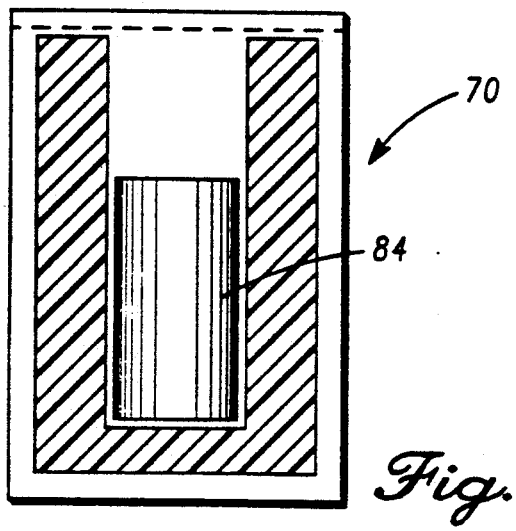
FIG. 6B illustrates an individual plastic bag containing a length of plastic tubing and FIG. 6C shows the bag of 6B with an identification label used to wrap the bag into conformity with the plastic tubing.
Figure 6C:
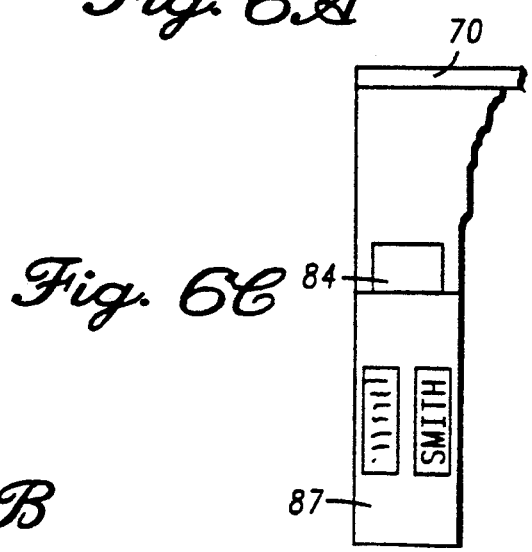

In another feature of the individual plastic bag 70 a semi-rigid element, such as plastic tubing 84, can be placed within the individual plastic bag 70 as shown in FIG. 6B. The fluid specimen can be introduced into the individual plastic bag 70 which is then sealed. An identification label 87 can also be wrapped around the individual plastic bag 70 which is thus conformed to the shape of the semi-rigid element. In the form illustrated in FIG. 6C the individual plastic bag 70 takes on a cylindrical shape enabling use as a test tube type structure which can be placed into conventional test tube receptacles of automatic analysis equipment (see FIG. 5). For such analysis procedures the top of the individual plastic bag 70 is cut open to allow access by a syringe to remove a fluid specimen for analysis or to add test chemicals to determine the presence of selected drugs. In addition, optical testing can be performed on the fluid specimen to ascertain the presence of selected drugs.

While preferred embodiments of the invention have been shown and described, it will be clear to those skilled in the art that various changes and modifications can be made without departing from the invention in its broader aspects as set forth in the claims provided hereinafter.

What is claimed is:

1. A multicompartment plastic bag for collection of a human fluid specimen for analysis, comprising:
   an upper bag section having an opening in said bag to receive said specimen collected from the human subject;
   a lower bag section at least partially open to said upper bag section for receiving said human fluid specimen, and thereafter said upper and lower bag sections sealed apart by nonreusable seals to prevent nondestructive access to said specimen and said lower bag section including separable subcompartments sealed by said nonreusable seals to prevent nondestructive access to said specimens with each of said bag sections and said sealed subcompartments providing separate redundant portions of said fluid specimen collected for analysis, at least one of said subcompartments including a dispensing spout element defined by heat seal lines in said lower bag section; and
   an identification element disposed on a surface of said plastic bag, said identification element including a writable area for entering information identifying the human donor and the chain of custody of each of said redundant portions of said fluid specimen.

2. A multicompartment plastic bag for receiving a human fluid specimen collected for analysis, comprising:
   an upper bag section having an opening in said bag to receive said specimen from the human subject;
   a lower bag section at least partially open to said upper bag section, and said plastic bag sealable to form nonreusable seals between said upper and lower bag sections with said upper and lower bag sections separable for providing separate sealed, redundant portions of said human fluid specimen for analysis; and
   said lower bag section further including a pouch element defined by plastic layers being discontinuous with the plastic sheets forming the basic structure of said plastic bag, said pouch element fillable with said human fluid specimen to provide an enlarged localized volume and an increased specimen optical path length enabling optical analysis of said fluid specimen, said pouch element further comprising at least one of a predetermined precise specimen volume and a predetermined precise specimen optical path length.

3. The plastic bag as defined in claim 2 wherein said upper bag section can be closed by heat sealing.

4. The plastic bag as defined in claim 2 further including holes punched along a perimeter seal line of said plastic bag, said holes allowing the hanging of said bag on storage rack and conveying of said bag for analytical processing.

5. A multicompartment plastic bag for receiving a human fluid specimen collected for analysis, comprising:
   an upper bag section having an opening to receive said specimen collected from the human subject;
   a lower bag section at least partially open to said upper bag section to receive said human fluid specimen collected from the human subject and said plastic bag sealable to form nonreusable seals between said lower bag section and said upper bag section after receiving said human fluid specimen, said upper and lower bag sections separable for providing sealed, separate portions of said human fluid specimen collected for analysis, at least one of said bag sections including an element, said element being one of a substantially rigid element or a semi-rigid element, protruding from a hole in one of said bag sections and said bag forming a seal with said protruding element; and
   means disposed within at least one of said upper and said lower bag sections for chemically reacting with said specimen after sealing said bag section containing said means for chemically reacting for subsequently performing an in situ analysis of said specimen.

6. A multicompartment plastic bag for receiving a human fluid specimen collected for analysis, comprising:
   an upper bag section having an opening to receive said specimen collected from the human subject; and
   a lower bag section at least partially open to said upper bag section and said plastic bag heat sealable to form nonreusable seals between said upper and lower bag sections after receiving said human fluid specimen, said upper and lower bag sections separable for providing sealed, separate redundant portions of said human fluid specimen collected for analysis and at least one of said upper and said lower bag sections further including an element, said element being at least one of a substantially rigid and a semi-rigid element disposed at least partly in a portion of said bag section therein, said element providing a predetermined shape for allowing analytical processing of said separate portions of said collected specimen by fitting said separated bag section portion containing said element into an instrument having a mating receptacle for receiving said element shape and said fitted, separate bag section portion.

7. The plastic bag as defined in claim 6 wherein said rigid element comprises plastic tubing enabling the fitting of said bag subcompartment into test tube shaped receptacles of said instrument.

8. A multicompartment plastic bag for collection of a fluid specimen for analysis, comprising:
   an upper bag section having an opening to receive said fluid specimen collected;
   a lower bag section at least partially open to and sealable from said upper bag section to form nonreusable seals therebetween, said upper and lower bag sections separable for providing separate, sealed redundant portions of said fluid specimen for analysis and at least one of said upper and said lower bag sections further including at least one of substantially rigid element and a semi-rigid element protruding from a hole in one of said bag sections and said bag forming a seal around said protruding rigid and/or semi-rigid element.

9. The plastic bag as defined in claim 8 wherein said element protrudes out of the bottom of said bag section and said plastic bag forms a tight seal around the exterior circumference of said element in the vicinity of the protrusion of said element from the inside of said plastic bag.

10. The plastic bag as defined in claim 8 wherein said element comprises at least one of a cylindrical shape, a conical funnel shape, a pipette shape and at least part of a spherical shape.

11. An individual plastic bag for selectively collecting an dispensing a biological fluid specimen, comprising:
   a heat sealable plastic bag having an opening; and
   a structural element within integral with said individual plastic bag, said structural element displaceable for selectively dispensing said drawing in said fluid specimen through an opening in said plastic bag.

12. The plastic bag as defined in claim 11 wherein said structural element comproses at least one of a pipette structure, a test tube structure and a cuvette.

13. The plastic bag as defined in claim 11 further including a wrapping label for wrapping said plastic bag about the shape of said displaceable component.

14. A plastic bag for receiving a fluid specimen collected for analysis, comprising:
   at least two sheets of plastic forming said plastic bag with said plastic sheets sealed together and said plastic bag having an opening to receive said fluid specimen; and
   a plurality of subcompartments in said plastic bag and said subcompartments at least partially open to receive said fluid specimen and nonreusable seals formed about each said subcompartment to prevent nondestructive access to redundant fluid specimens in each of said plurality of subcompartments, a structural element integral with said plastic bag and displaceable for selectively dispensing and drawing in said fluid specimen through an opening in the plastic bag.

15. A plastic bag for selectively collecting and dispensing a biological fluid specimen, comprising:
   said plastic bag sealable to form a sealed bag with at least one sealed compartment and having an opening for receiving said biological fluid specimen; and
   a structural element of said at least one compartment wherein said structural element is integral with said plastic bag and displaceable for selectively dispensing and drawing in said fluid specimen through an orifice in said plastic bag.

* * * * *

UNITED STATES PATENT AND TRADEMARK OFFICE
CERTIFICATE OF CORRECTION

PATENT NO. : 5,084,041

DATED : January 28, 1992

INVENTOR(S) : Oxley, L. Thomas & Morriseau, Virginia C.

It is certified that error appears in the above-identified patent and that said Letters Patent is hereby corrected as shown below:

Column 11, line 9 "an" should be --and--;

line 11 add --and-- after "within".

Signed and Sealed this

Tenth Day of August, 1993

*Attest:*

MICHAEL K. KIRK

*Attesting Officer*     *Acting Commissioner of Patents and Trademarks*